United States Patent [19]

Leong et al.

[11] Patent Number: 5,280,792
[45] Date of Patent: Jan. 25, 1994

[54] METHOD AND SYSTEM FOR AUTOMATICALLY CLASSIFYING INTRACARDIAC ELECTROGRAMS

[75] Inventors: Philip H. W. Leong, Willoughby; Marwan A. Jabri, Hunters Hill, both of Australia

[73] Assignee: The University of Sydney, Sydney, Australia

[21] Appl. No.: 947,337

[22] Filed: Sep. 18, 1992

[30] Foreign Application Priority Data

Sep. 20, 1991 [AU] Australia .................. PK8478

[51] Int. Cl.⁵ .................................. A61B 5/0452
[52] U.S. Cl. .................................. 128/702; 395/22; 395/26
[58] Field of Search ............... 128/702–705, 128/419; 395/22, 26, 27

[56] References Cited

U.S. PATENT DOCUMENTS

| | | |
|---|---|---|
| 3,755,783 | 8/1973 | Astorjian et al. .................. 128/702 |
| 3,829,766 | 8/1974 | Herz ................................ 128/704 |
| 4,453,551 | 6/1984 | Anderson et al. ................. 128/704 |
| 4,912,653 | 3/1990 | Wood ............................... 395/26 |
| 4,933,872 | 6/1990 | Vandenberg et al. .............. 395/26 |
| 5,058,599 | 10/1991 | Andersen ......................... 128/705 |
| 5,086,772 | 2/1992 | Larnard et al. ................... 128/419 D |
| 5,092,343 | 3/1992 | Spitzer et al. ..................... 395/22 |

Primary Examiner—William E. Kamm
Attorney, Agent, or Firm—Dressler, Goldsmith, Shore & Milnamow, Ltd.

[57] ABSTRACT

The application is directed to a method for automatically classifying intracardiac electrograms, and a system for performing the method. In a further aspect, it concerns an implantable cardioverter defibrillator which incorporates the system and uses the method to monitor cardiac activity and deliver appropriate treatment. The method uses a combination of timing analysis and pattern matching using a neural network in order to correctly classify the electrograms. This technique allows both changes in rate and morphology to be taken into account.

19 Claims, 11 Drawing Sheets

N.B. DISSOCIATED MEANS PP/RR > 1.5

METHOD AND SYSTEM FOR AUTOMATICALLY CLASSIFYING INTRACARDIAC ELECTROGRAMS

TECHNICAL FIELD

This invention concerns a method and system for automatically classifying intracardiac electrograms.

BACKGROUND ART

The automatic implantable cardioverter defibrillator (AICD or "implantable cardioverter defibrillator") is a device used in the treatment of a class of patients prone to life threatening tachycardias. Currently, implantable cardioverter defibrillators classify signals derived from a single channel; a ventricular sensing electrode. Many single channel intracardiac electrographic classification methods have been proposed, including frequency domain analysis, gradient pattern detection, sequential testing, median frequency, correlation waveform analysis, the Bin area method and neural networks. However, they have been found to be unreliable in their classification of many common tachycardias. This often causes inappropriate therapy to be delivered by the implantable cardioverter defibrillator. Many of the incorrect classifications made by current devices are caused by the overlap of heart rate ranges between sinus tachycardia (ST), supraventricular tachycardia (SVT) and ventricular tachycardia (VT).

Previous work on the classification of intracardiac electrogram signals derived from two channels have concentrated on the analysis of timing sequences. These studies show that the addition of an atrial sensing electrode can greatly improve the reliability of the classification, when compared with classification using a single intracardiac lead.

The improvements are especially marked in differentiating between supraventricular tachycardia (SVT), sinus tachycardia (ST), and ventricular tachycardia (VT). Tachycardias with timing similar to normal sinus rhythm (NSR) such as ventricular tachycardia with 1.1 retrograde conduction (VT 1:1) cannot be identified using these techniques. However, morphological considerations can often resolve this distinction.

SUMMARY OF THE INVENTION

According to a first aspect of the present invention the invention, there is provided a method for automatically classifying intracardiac electrograms, comprising the steps of:

(a) extracting timing parameters from a first input signal representing an electrogram, and deriving from them a first output signal;

(b) deriving a second output signal, which is a measure of the electrogram's likeness to an arrhythmia, from a second input signal (which may be the same as the first) representing the electrogram, using a neural network; and (c) indicating the classification taking into account the first output signal derived in step (a), and the second output signal derived in step (b).

Preferably the first input signal represents ventricular activity in a first channel and atrial activity in the second channel.

Also preferably the second input signal represents ventricular activity.

Optionally in step (a) the phase difference between the ventricular channel and the atrial channel is extracted, and if the ratio of this number to the ventricular period is less than a predetermined amount the first output signal indicates normal sinus rhythm.

Optionally in step (a) the periods of the ventricular channel and the atrial channel are extracted, and if the ratio of the period of the atrial waveform to the period of the ventricular waveform is greater than a predetermined amount, then atrial-ventricular dissociation is indicated by the first output signal.

Optionally in step (a) the ventricular channel period, the atrial channel period, and the phase difference between the ventricular and atrial channels are extracted and;

if the ventricular period is less than a first threshold the first output signal indicates ventricular fibrillation;

if the ventricular period is between the first threshold and a second, higher, threshold and if the ratio of the period of the atrial waveform to the period of the ventricular waveform is greater than a predetermined amount then the first output signal indicates ventricular fibrillation;

if the ventricular period is greater than the second threshold and if the ratio of the period of the atrial waveform to the period of the ventricular waveform is greater than a predetermined amount then the first output signal indicates ventricular tachycardia; otherwise, if the atrial period is found to be less than a third threshold, between the first and second, then the first output signal indicates supraventricular tachycardia;

if the ratio of the phase difference between the ventricular channel and the atrial channel, and the ventricular period is less than a predetermined amount the first output signal indicates then normal sinus rhythm;

otherwise the first output signal indicates supraventricular tachycardia.

Optionally in step (b) the neural network has been trained to detect normal sinus rhythm and ventricular tachycardia with 1:1 retrograde conduction, and the second output signal is a measure of the electrogram's likeness to ventricular tachycardia with 1:1 retrograde conduction.

Optionally if the second output signal indicates a measure of more than a predetermined value of likeness to 1:1 retrograde conduction then the classification indicated in step (c) is ventricular tachycardia with 1:1 retrograde conduction.

Optionally the method includes the further step of only providing a classification indication if a predetermined number of the immediately preceding classifications indicated in step (c) are the same.

Preferably step (c) comprises indicating the classification indicated by the first output signal, if it indicates ventricular fibrillation arrhythmia; otherwise indicating the classification indicated by the second output signal if the measure of likeness to the arrhythmia is greater than a predetermined value, or indicating the classification indicated by the first output signal if the measure of likeness is less than the predetermined value.

Embodiments of the invention may be employed for classifying a wide range of arrhythmias and may be used to differentiate between sinus tachycardia (ST), normal sinus rhythm (NSR), normal sinus rhythm with bundle branch block, sinus tachycardia with bundle branch block, atrial fibrillation, various supraventricular tachycardias (SVT), ventricular tachycardia (VT), ventricular tachycardia with 1:1 retrograde conduction (VT 1:1) and ventricular fibrillation (VF).

Using embodiments of the invention correct classification is possible even when there are numerous ventricular ectopic beats, fusion beats, noise and other artefacts. Examining the sequence of outputs of the timing and morphology, sequences of patterns such as bigeminy and trigeminy can also be recognised using syntactic parsing techniques (e.g. regular expressions implemented using a finite state machine). Also, correct classification can be achieved on patients who are on a variety of medications.

According to a second aspect the invention provides a system for automatically classifying intracardiac electrograms comprising:

timing classification means to receive a first input signal representing an electrogram and deriving a first output signal from timing parameters extracted from the first input signal;

a neutral network to receive a second input signal (which may be the same as the first) representing the electrogram, and deriving a second output signal which is a measure of the electrogram's match to an arrhythmia; and decision means operative, taking into account the first output signal from the timing classification means and the second output signal from the neural network, to indicate the classification.

Preferably the neutral network is a multi-layer perceptron.

Preferably the neural network has been trained to detect normal sinus rhythm and ventricular tachycardia with 1:1 retrograde conduction, and the second output signal is a measure of the electrogram's likeness to ventricular tachycardia with 1:1 retrograde conduction.

Preferably the first input signal represents ventricular activity in a first channel and atrial activity in a second channel.

Preferably the second input signal represents ventricular activity.

Preferably the decision means indicates the classification indicated by the second output signal when the measure of likeness to the arrhythmia is greater than a predetermined value.

Preferably the decision means indicates the classification indicated by the first output signal if ventricular fibrillation arrhythmia is indicated by the timing classification means; otherwise the decision means indicates the classification indicated by the second output signal when the measure of likeness to the arrhythmia is greater than a predetermined value, or the classification indicated by the first output signal when the measure of likeness is less than the predetermined value.

Preferably the system is embodied as an implantable cardioverter defibrillator. The inputs are raw intracardiac electrogram signals and the output is the recommended implantable cardioverter defibrillator therapy. For instance, the implantable cardioverter defibrillator may classify the arrhythmia into four groups: normal sinus rhythm (NSR), supraventricular tachycardias (SVT), ventricular tachycardia (VT) and ventricular fibrillation (VF), depending on whether the therapy required.

BRIEF DESCRIPTION OF THE DRAWINGS

The present invention will now be described by way of example only, with reference to the accompanying drawings, in which.

BEST MODE FOR CARRYING OUT THE INVENTION

Figure 1:
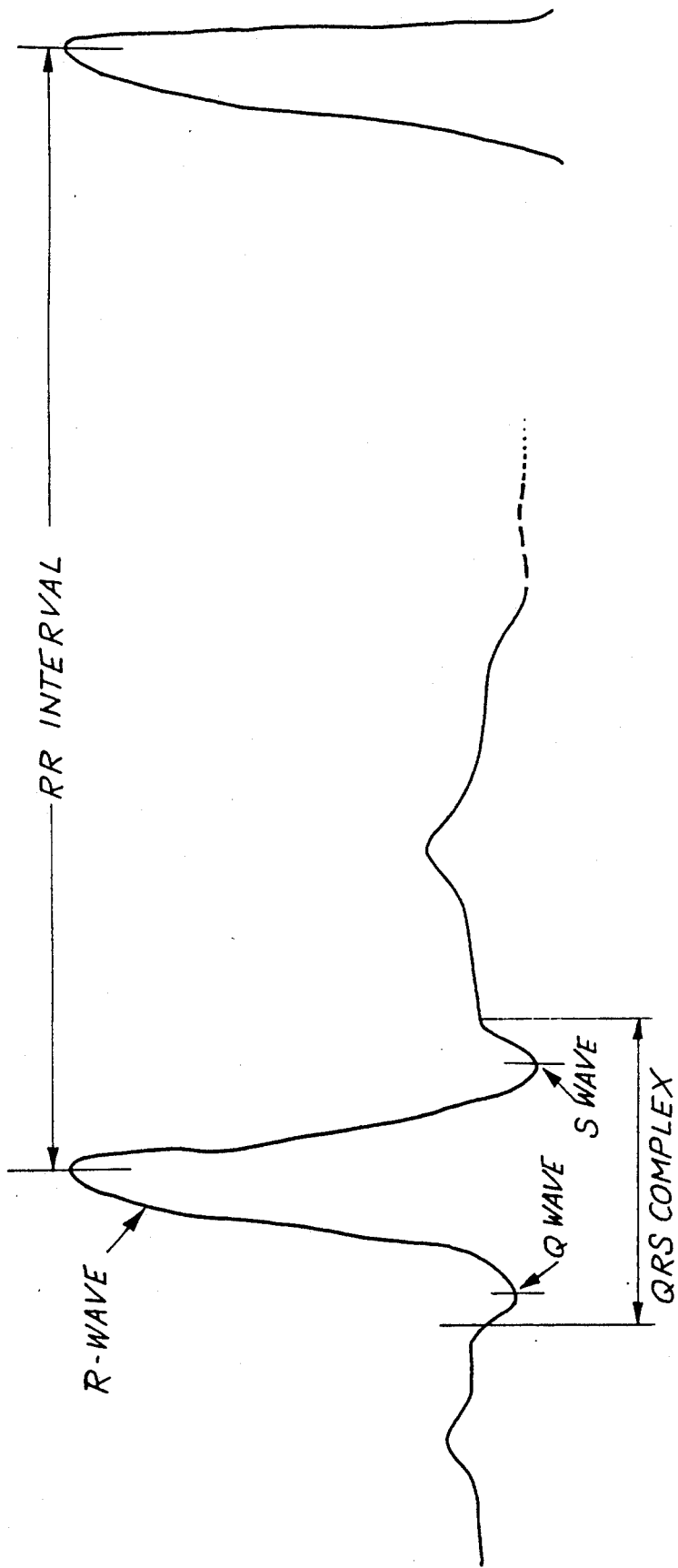
FIG. 1 is a representation of a typical electrocardiogram.

Referring now to FIG. 1, a typical ventricular waveform from an electrocardiogram has a recurring waveform in which the trained eye can identify a spike known as the R wave, on either side of which are two smaller inverted spikes known as the Q and S waves respectively. Taken together the region of the waveform from the beginning of the Q wave to the end of the S wave is known as the QRS complex, and this region has importance for the classification of tachycardias. In the atrial waveform, the spike is known as the P wave.

Figure 2:
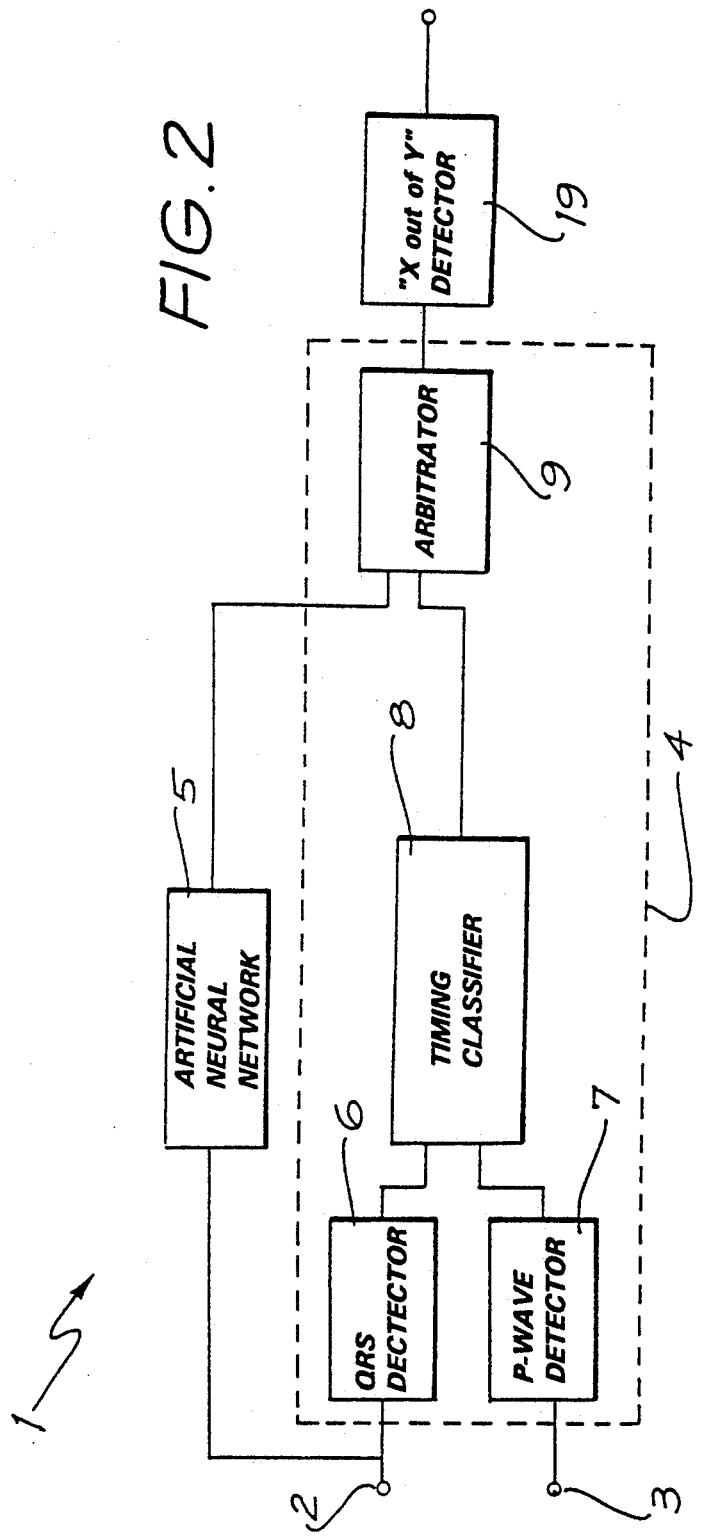
FIG. 2 is a block diagram of a system embodying the present invention.

Referring now to FIG. 2, system 1 comprises a first input terminal 2 connected, in use, to a ventricular sensing electrode and second input terminal 3 connected, in use, to an atrial sensing electrode. Each input terminal is associated with an input channel to a timing network 4, and in addition input terminal 2 is connected to an artificial neural network 5 arranged in parallel with the timing network 4.

The timing network 4 comprises a QRS detector 6 for the ventricular channel, and a p wave detector 7 for the atrial channel. These detectors compare the slope of the differentiated QRS (or p) signal with an adaptive threshold to identify a fudicial point using a refractory period of 80 ms. From these detectors timing classifier 8 derives parameters indicating the periods of the ventricular (RR) and atrial (pp) signals, and a measure of the phase difference between them; that is the time between the R wave of the ventricular waveform and the P wave of the atrial waveform, known as the AV internal, or the PR interval An arbitrator 9 selects either the output from the artificial neural network 5 or the timing classifier 8.

Figure 3:
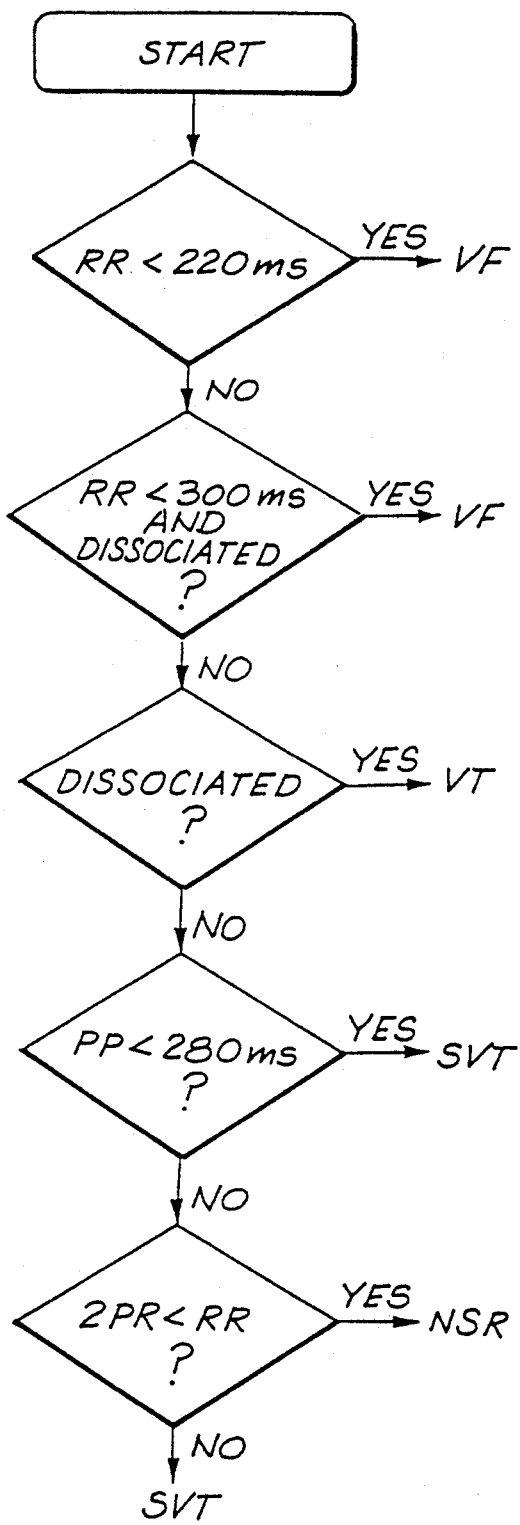
FIG. 3 is a flow chart of the timing based decision logic of the timing classifier forming part of the embodiment of FIG. 2.

In the timing classifier 8 a simple decision tree is used to perform a first order classifications of the signals based on the timing information. A flow chart of the logic used is shown in FIG. 3 and will now be described.

If the ventricular waveform period is small enough (RR<220 mS) then the signal is classified as ventricular fibrillation (VF), although it may also be a very fast ventricular tachycardia. This is acceptable since a very fast ventricular tachycardia is given the same treatment by a implantable cardioverter defibrillator as ventricular fibrillation (VF).

The next case is the slower "fast ventricular tachycardia" rhythm which requires both a reasonably fast rate (220 mS<RR<300 mS) and atrial-ventricular (AV) dissociation. Note that a non-standard definition of the term "dissociation" is used, the rhythm being considered dissociated if twice the atrial period is greater than three times the ventricular period (pp*2>RR*3); or alternatively, if the instantaneous ventricular rate is more than 1.5 times faster than the instantaneous atrial rate. This is also classified as ventricular fibrillation (VF).

If dissociation is present but the rhythm is not fast enough to be a fast ventricular tachycardia the signal is classified as ventricular tachycardia (VT).

The atrial waveform period is then checked for a class of fast atrial rhythms, such as atrial flutter and atrial fibrillation, (PP<280 mS) which are all classified as supraventricular tachycardia (SVT).

A normal rhythm (NSR) is characterised by the atrial P wave occurring before the ventricular R wave, and a check is made for the ratio of the phase difference between the ventricular channel and the atrial channel, and the ventricular period; if this ratio is less than a predetermined amount normal sinus rhythm is indicated.

The final statement classifies all other rhythms as being supraventricular tachycardia (SVT). This classifies the true supraventricular tachycardia correctly, as well as catching any rhythms which are not normal sinus rhythm (NSR), ventricular tachycardia (VT) or ventricular fibrillation (VF), enabling the unclassified rhythms to be logged by the system.

Note that in all cases the timing logic is patient independent. Also, analogue to digital conversion is not required even though the timing based algorithm is processed digitally.

Figure 4:
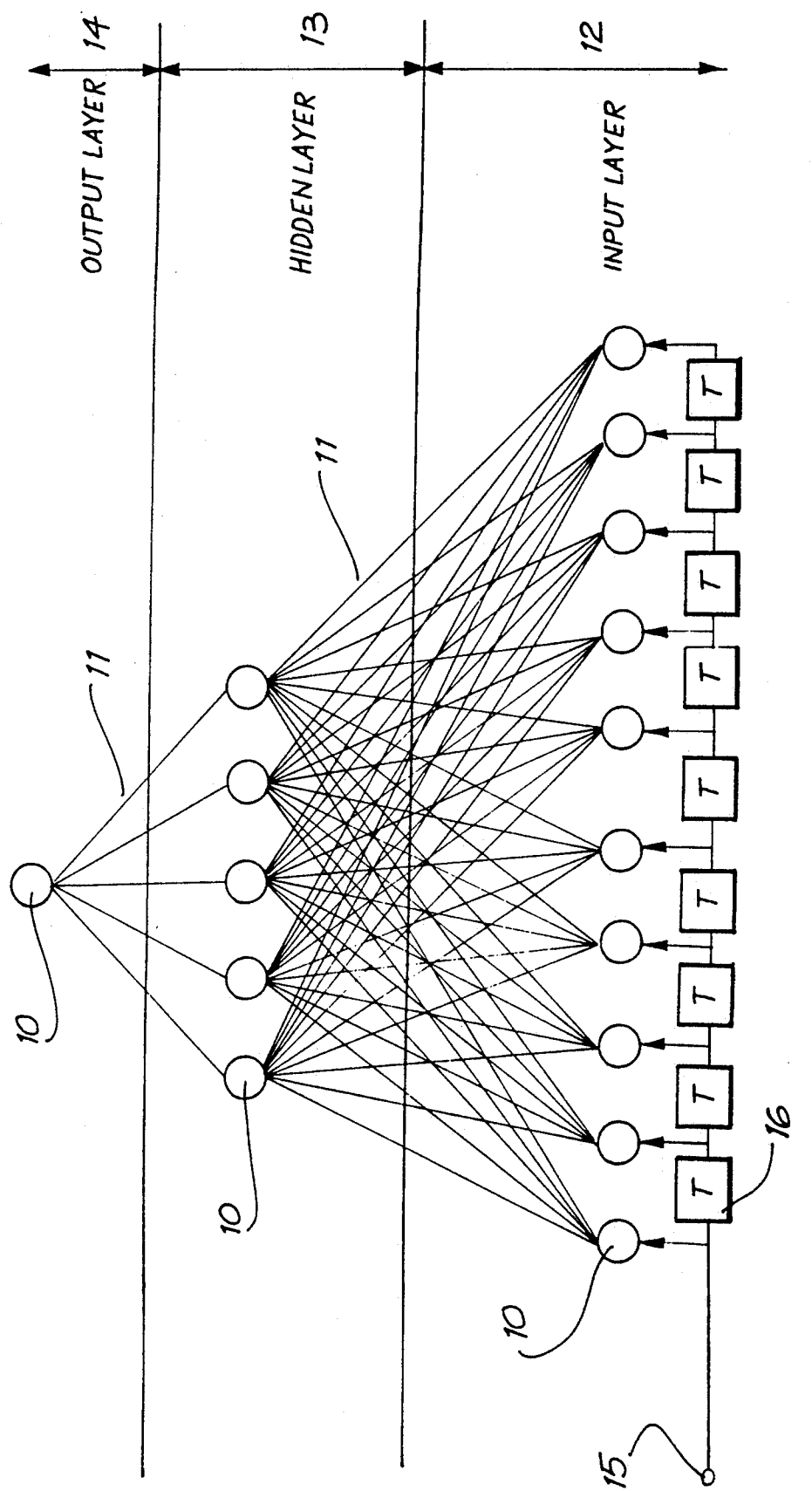
FIG. 4 is a block diagram of a neural network forming part of the embodiment of FIG. 2.

In parallel with the timing logic, the artificial neural network 5 is used on a sequence of input samples to identify the morphology. The artificial neural network 5 will now be described with reference to FIG. 4.

The network has an architecture for computing inspired by biological neural systems. It consists of a large number of simple computational elements (neurons) 10 operating in parallel. The neurons are connected through programmable synaptical connections (called synapses or weights) 11 which modify tha strength of the connections between neurons.

The connection topology of the neurons and synapses form the architecture of the neural network. The architecture chosen for this embodiment used is a three-layer perceptron, meaning that the neurons are organised into three-layers (an input layer 12, a hidden layer 13 and an output layer 14), any particular neuron being connected to all neurons in the layer above. The network operates in a strictly feedforward manner with the signals arriving at input terminal 15 passing through a series of time delays 16 and then to neurons in the input layer before propagating through the hidden layer 12 to the output layer 14 via the weights 12 (represented by the lines connecting the neurons together).

The input to each neuron 10 is the weighed sum of the outputs of all neurons in the previous layer, and the output is the sigmoidal function $f(x) = 1.0/(1-e^{-x})$. Except for the neurons in the input layer which have the identity transfer function $f(x) = x$.

Figure 5:
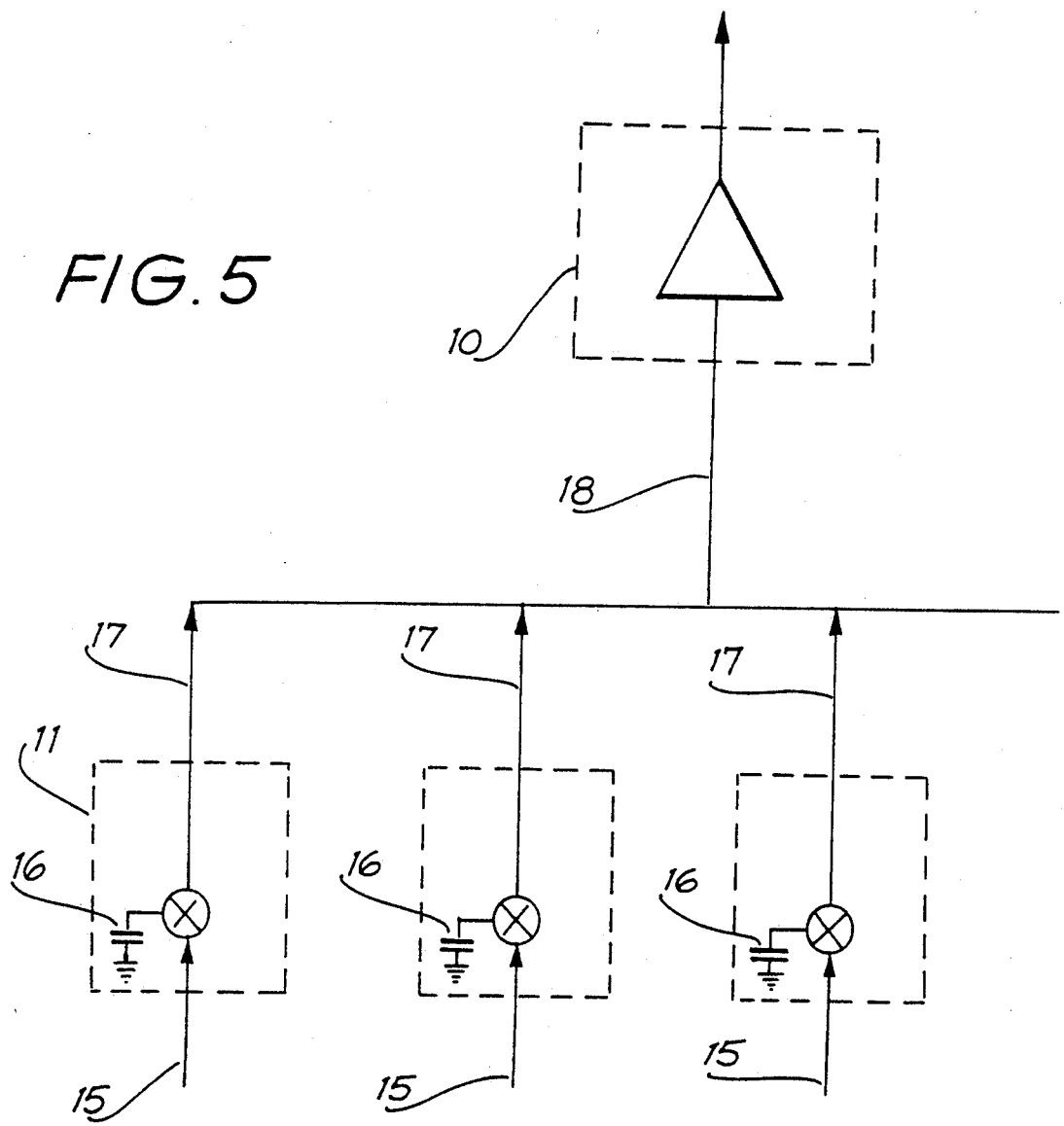
FIG. 5 is a detail of the neural network of FIG. 4.

FIG. 5 shows a neuron and synapse in more detail. The output 15 from neurons in one layer are applied as inputs to the synapses 11 where they are multiplied, using analogue multipliers, by weights stored on capacitors 16. The weights are periodically refreshed, but this can be done at very low frequency. The outputs 17 from the synapses are summed 18, by summing currents along a wire, and then applied as the input to a neuron in the next layer.

The neuron function is provided by converting the current to voltage using the non-linear characteristics of transistors. All transistors are operated in the subthreshold region and draw currents of the order of 10 nanoamps. Measured power consumption of a recently designed neural network chip using this technology, which has 50 weights and 8 neurons, is approximately 60 microwatts (this figure includes interface circuitry). Further savings in power can be achieved by turning parts of the neural network off when not being used.

Mathematically, the output of a neuron in layer $l+1$ is given by $$a_i^{(l+1)} = f\left(\sum_{j=1}^{N_l} W_{ij} a_j^l\right)$$

where $w_{ij}$ represents the weights, $a_j^l$ is the output of the jth neurons in the lth layer and $N_l$ is the number of neurons in the lth layer.

A three layer perceptron classifier can, by virtue of the non-linearities of the neurons, produce arbitrarily complex mappings from the input samples to the output classes. Without the non-linearity of the neurons only linear mappings could be achieved.

"Training" of an artificial neural network involves finding a set of weight values which map a set of input vectors to the desired set of output vectors. In this embodiment, training was achieved using the back-propagation algorithm. Backpropagation simply performs minimisation of the multidimesional error function $$e(w) = \frac{\left(\sum_{p=1}^{P}(d_p - \theta_p(w))^2\right)}{P}$$

where p represents input patterns in the training set, P is the number of training patterns, w is a vector of weight values, $\theta_p$ is the desired output, and $\theta_p$ is the output of the neural network when the pth training pattern is applied to the inputs. Backpropagation uses the method of steepest (gradient) descent, weights being updated by the formula $$\Delta w_{ij} = -\alpha \frac{\partial e}{\partial w_{ij}}$$

where $\Delta w_{ij}$ is the change to be applied to the weights ($w_{ij} \leftarrow w_{ij} + \Delta w_{ij}$), $\delta e/\delta w_{ij}$ is the partial derivative or e with respect to $w_{ij}$, and $\alpha$ is a constant. For $\alpha$ sufficiently small the error function of the new w will always be less than or equal to the error function for the previous value of w and hence we can reduce the error until we reach a minima. This minima, in general, is not the global minimum, but for a wide class of problems the algorithm is able to find a satisfactory solution.

After training, the network is used to generalise, the weights $w_{ij}$ being fixed in value. New inputs are applied to the neural network and patterns which are "similar" to the trained input patterns give similar outputs to the training examples.

Neural networks have been successfully applied to pattern matching problems and, in contrast to correlators, they can store more than one pattern as well as solve non-linear problems. In addition micropower implementations of neural networks have been demonstrated.

In a typical training set, the network is trained so the normal sinus rhythm (NSR) has the output value 0. Data about the abnormal morphology to be identified is collected from an electrophysiological study (EPS) of the patient, or long term intracardiac recordings, and the network trained to give it the output value 1.

During classification, if the output becomes greater than 0.9 a decision is taken by arbitrator 9 to use the morphological classification instead of the timing classification.

For instance, the system may be advantageously employed to identify patients having ventricular tachycardia rhythm with 1:1 retrograde conduction (VT 1:1).

Figure 6:
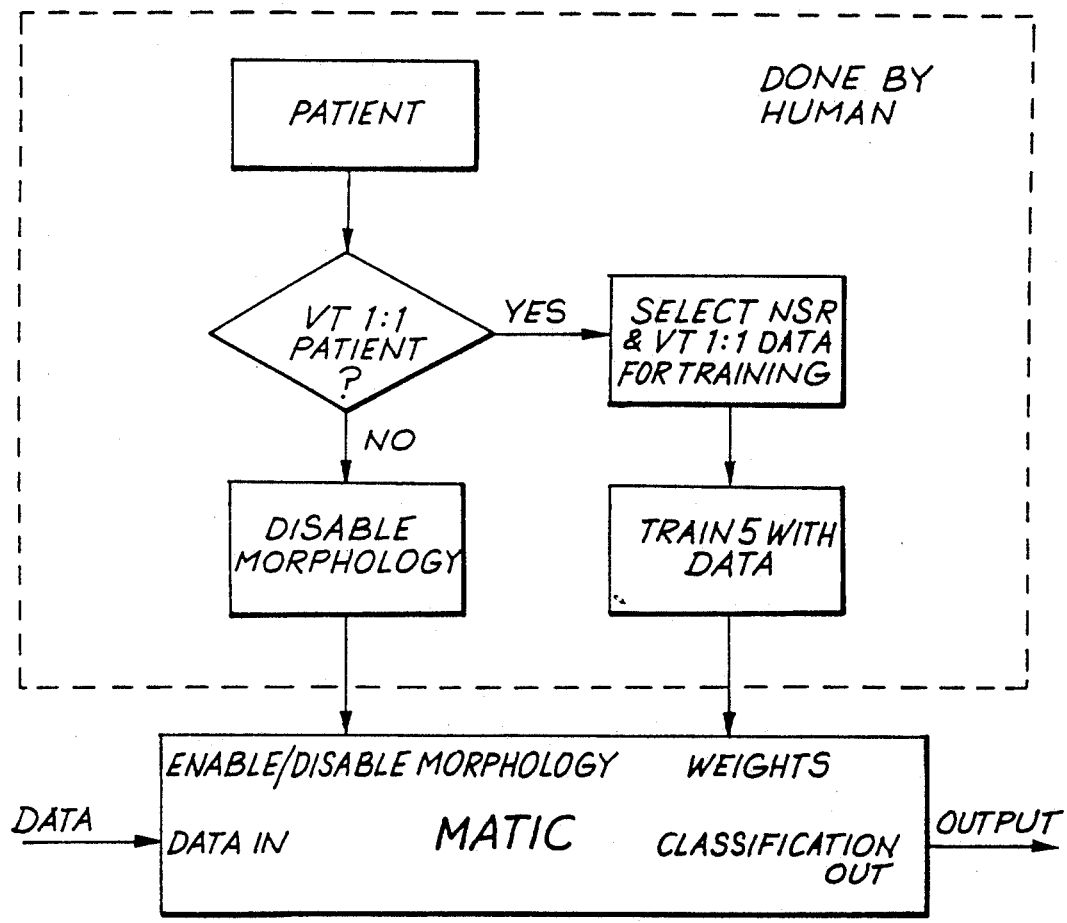
FIG. 6 is a flow chart of a configuration procedure for an embodiment of the invention.

In order to perform classification, a human must first configure the system. A flowchart of this configuration process is shown in FIG. 6. Configuration involves deciding if the patient is a VT 1:1 patient or not (this decision is usually guided by EPS) and if so, four normal sinus rhythm and four of the abnormal ventricular tachycardia 1:1 QRS complexes are selected (by a human) for that patient to serve as templates for the neural network morphology classifier 5. During training the desired output of the normal sinus rhythm complexes is made equal to 0.0 and the desired output of the abnormal ventricular tachycardia complexes is made equal to 1.0.

The neural network then operates in parallel with the timing logic, using the weights obtaining through training, to identify an abnormal ventricular tachycardia which is not dissociated, but does have a different QRS morphology to the patient's normal sinus rhythm.

The output of the neural network is a single number, between 0.0 and 1.0, indicating the degree with which the input value matches the stored patterns (much like the correlation coefficient in correlation waveform analysis).

Inputs to the neural network were 10 sampled points (sampling rate 125 Hz) from the ventricular channel centered about the R wave of the QRS complex (using the QRS detector). Originally, 20 inputs were used at the 250 Hz data rate, and the network was found to produce the correct outputs. The same window size was then applied at 125 Hz (i.e. 80 ms at 125 Hz is 10 samples) and this was found to produce the same results. The halving of the number of input neurons nearly halves the computational complexity of the neural network. Five hidden layer neurons were used as this is the smallest value which produced the correct results.

The arbitrator 9 arbitrates between the output of the timing logic and the output of the morphology classifier to produce single output class. The simple relation used is

| Class = VF | if timing logic output is VF |
| Class = VT | if neural network output > 0.9 |
| Class = timing logic output | otherwise |

After configuration, the system is fully automatic, taking electrocardiogram data as inputs and producing NSR, SVT, VT and VF classifications as output.

The output classifications are then passed to an "X out of Y" detector 19 which outputs a final classification only if 5 of the last 6 output classes of the arbitrator 9 are the same. If this criterion is not met, no output is produced. This X out of Y function serves to average the classifier decisions over time, removing incorrect classifications due to ectopic beats, fusion beats and artefacts. Note that this technique delays classification for at least 5 QRS complexes from the onset of the tachycardia. It is possible that a particular rhythm such as bigeminy can cause the classifier to produce alternating decisions and the X out of Y detector will never produce an output. This problem has not yet been addressed however, it should not be difficult to use syntactic parsing technique in place of the X out of Y detector in order to recognise such conditions.

EXAMPLES

Intracardiac electrograms were recorded during electrophysiological studies (EPS) at two different hospitals.

Either two or three temporary catheters were placed under fluoroscopic guidance in the right ventricular apex (RVA), the high right atrium (HRA) and sometimes on the His bundle (HIS) of the patient. Both bipolar and quadripolar catheters were used, although these differed between hospitals and patients.

During the study, signals from the intracardiac leads were recorded on a cassette data recorder after they were bandpass filtered through an isolation amplifier (0.5 to 100 Hz). The tapes were later played back through a 100 Hz anti-aliasing filter and digitised at 1000 Hz with either 12 bit or 16 bit accuracy. At the other hospital, the signals were bandpass filtered (0.5-150 Hz) and directly digitised at 1000 Hz 16 bits. The data were then downsampled to 250 Hz for use in the experiment.

In order to induce sinus tachycardia, a standard or modified Bruce treadmill test was performed in some patients. Some patients also received amidarone, captopril, frusemide or disopyramide before or during the electrophysical study.

The patients used had a wide variety of arrhythmia including sinus tachycardia, normal sinus rhythm, normal sinus rhythm with bundle branch block, sinus tachycardia with bundle branch block, atrial fibrillation, various supraventricular tachycardias, ventricular tachycardia, ventricular tachycardia with 1:1 retrograde conduction and ventricular fibrillation.

Within these arrhythmia, there were also numerous ventricular ectopic beats, fusion beats, noise and other artefacts. The tachycardias were classified into the most suitable subclasses by human experts and these classifications confirmed by other human experts.

The classifier maps the subclasses into four "superclasses": normal sinus rhythm (NSR), supraventricular tachycardia (SVT), ventricular tachycardia (VT) and ventricular fibrillation (VF), which correspond to the available treatments in an implantable defibrillator. For supraventricular tachycardia (SVT), the implantable defibrillator will either pace the atrium or simply log the fact that supraventricular tachycardia has occurred; for ventricular tachycardia it will pace the ventricle and then defibrillate if the ventricular tachycardia is not broken; and for ventricular fibrillation, defibrillation is performed.

The "confusion matrix" in Table 1 presents the results of the study, entries representing the number classifications.

TABLE 1

| Subclass | Class | Regions | NSR | SVT | VT | VF |
|---|---|---|---|---|---|---|
| NSR | NSR | 64 | 5605 | 4 | 2 | 0 |
| ST | NSR | 10 | 1535 | 24 | 2 | 1 |
| SVT | SVT | 9 | 0 | 1022 | 0 | 0 |
| AT | SVT | 2 | 0 | 52 | 0 | 0 |
| AF | SVT | 3 | 0 | 165 | 0 | 0 |
| VT | VT | 9 | 0 | 0 | 332 | 0 |
| VT 1:1 | VT | 10 | 2 | 0 | 1253 | 0 |
| VF | VF | 6 | 0 | 0 | 2 | 196 |
| VTF | VF | 9 | 0 | 2 | 0 | 116 |

The system output classes appear in the columns of the matrix and human classifications appear in rows. The subclass classification made by the human is mapped to an appropriate superclass (as shown in the first two columns of the table) so that the performance of the system for various tachycardias can be determined. As an example, the second row of Table 1 shows that the database held 10 regions (stable rhythms) of subclass "ST" (superclass "NSR"). The system produced 1562 outputs for these (ST) regions, and of these, 1535 were NSR, 24 were SVT, 2 were VT and 1 was VF. Note that 99.6% of the classifications are correct.

As discussed earlier, the difficult classifications are those between sinus tachycardia (ST), supraventricular tachycardia (SVT), ventricular tachycardia (VT) and ventricular tachycardia with retrograde conduction (VT 1:1). FIGS. 7 to 10 show typical waveforms analysed by the present classifier. The human classification (made without any knowledge of the computer classification) is on the topmost of the screen, and the row of classifications just underneath are those made by the embodiment. On the bottom "INFO" line, the number shows the time between the two vertical lines which appear on the screen. These (if used) measure timings of interest. The numbers which appear in the middle of the ICBG waveform is the sample number, the sample period being 4 ms.

Figure 7:
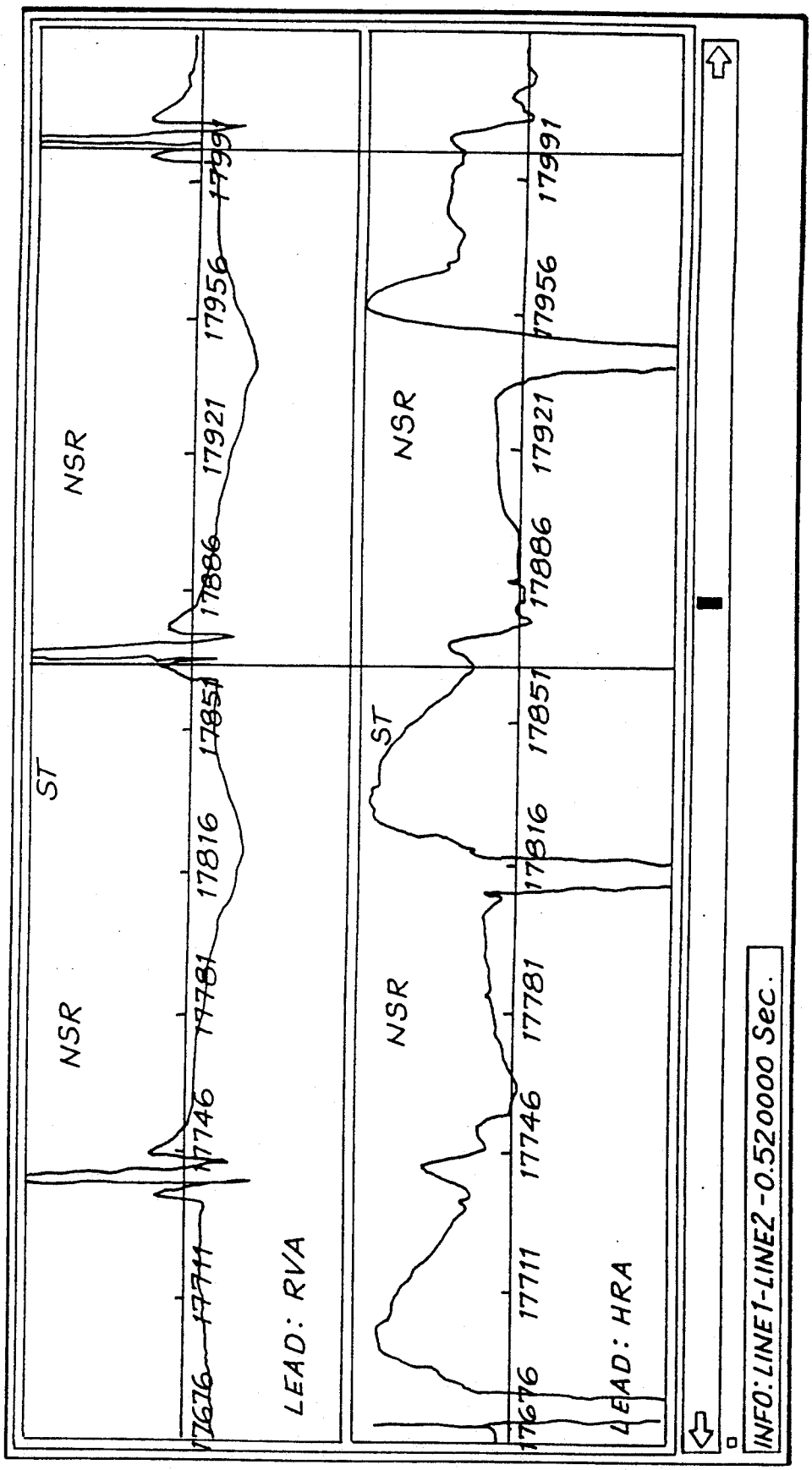
FIG. 7 is a representation of an electrocardiogram showing sinus tachycardia rhythm (normal conduction)

The sinus tachycardia in FIG. 7 is recognised correctly as normal sinus rhythm (a superclass which includes NSR and ST) because the embodiment considers it to have normal timing whereby atrial depolarizations cause the ventricular depolarizations (2PR<RR).

Figure 8:
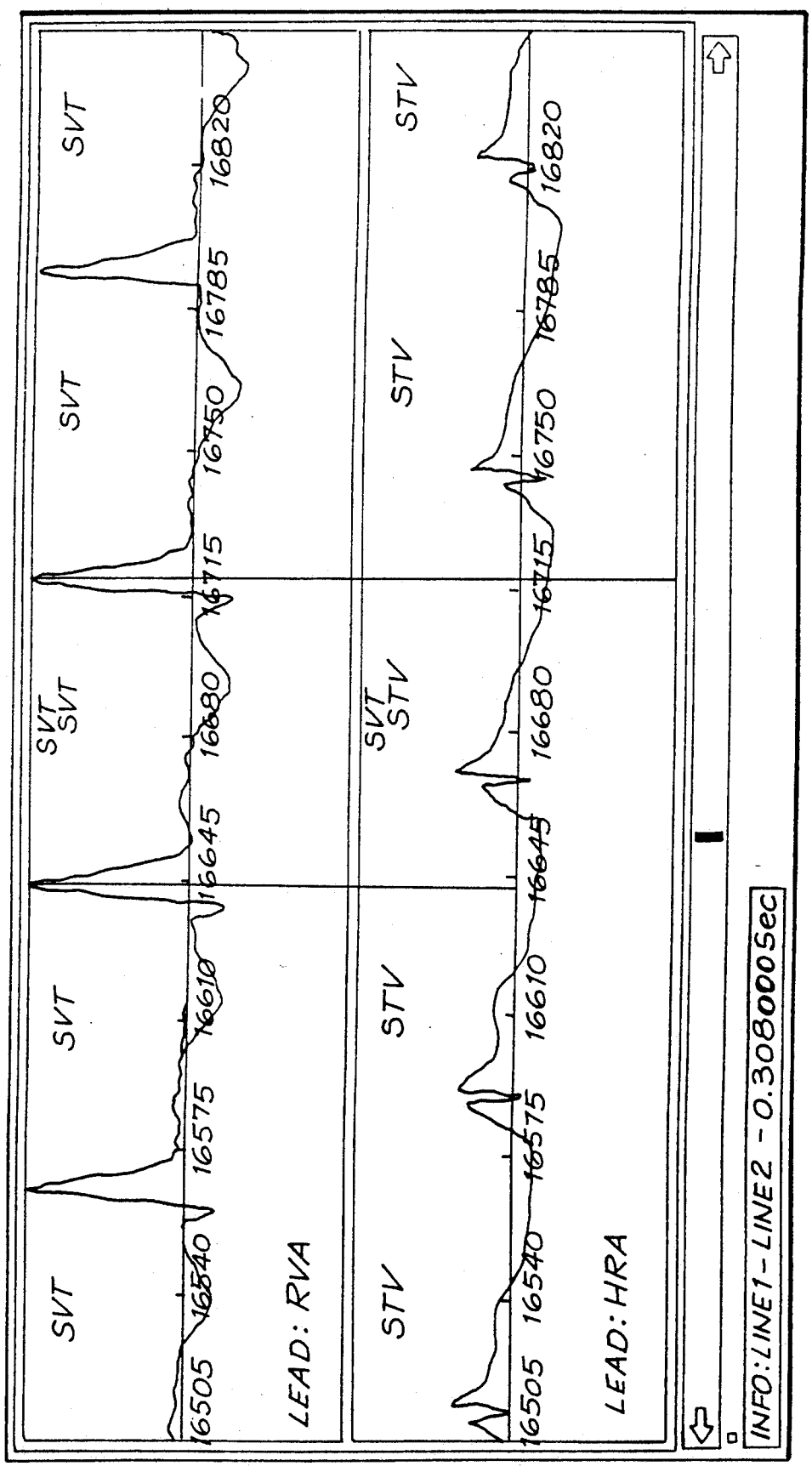
FIG. 8 is a representation of an electrocardiogram showing supraventricular tachycardia rhythm.

In FIG. 8, the PR interval is very long (2PR>RR) and the rhythm is classified as supraventricular tachycardia.

Figure 9:
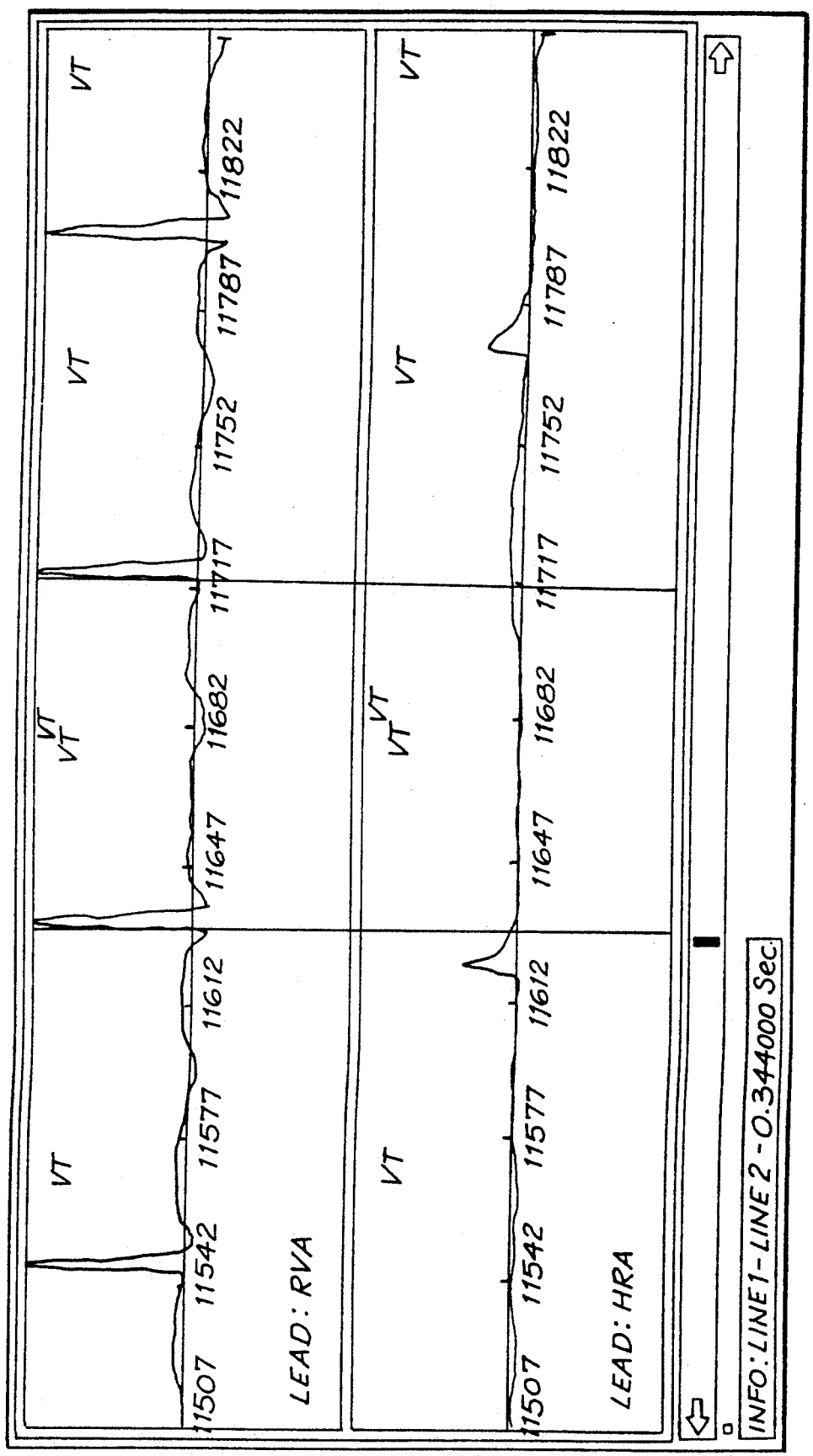
FIG. 9 is a representation of an electrocardiogram showing ventricular tachycardia rhythm.

In FIG. 9, AV dissociation is present and the tachycardia is classified as ventricular tachycardia. Note that although AV dissociation is easy to observe on two leads, it is often impossible to distinguish using only the ventricular lead.

Figure 10:
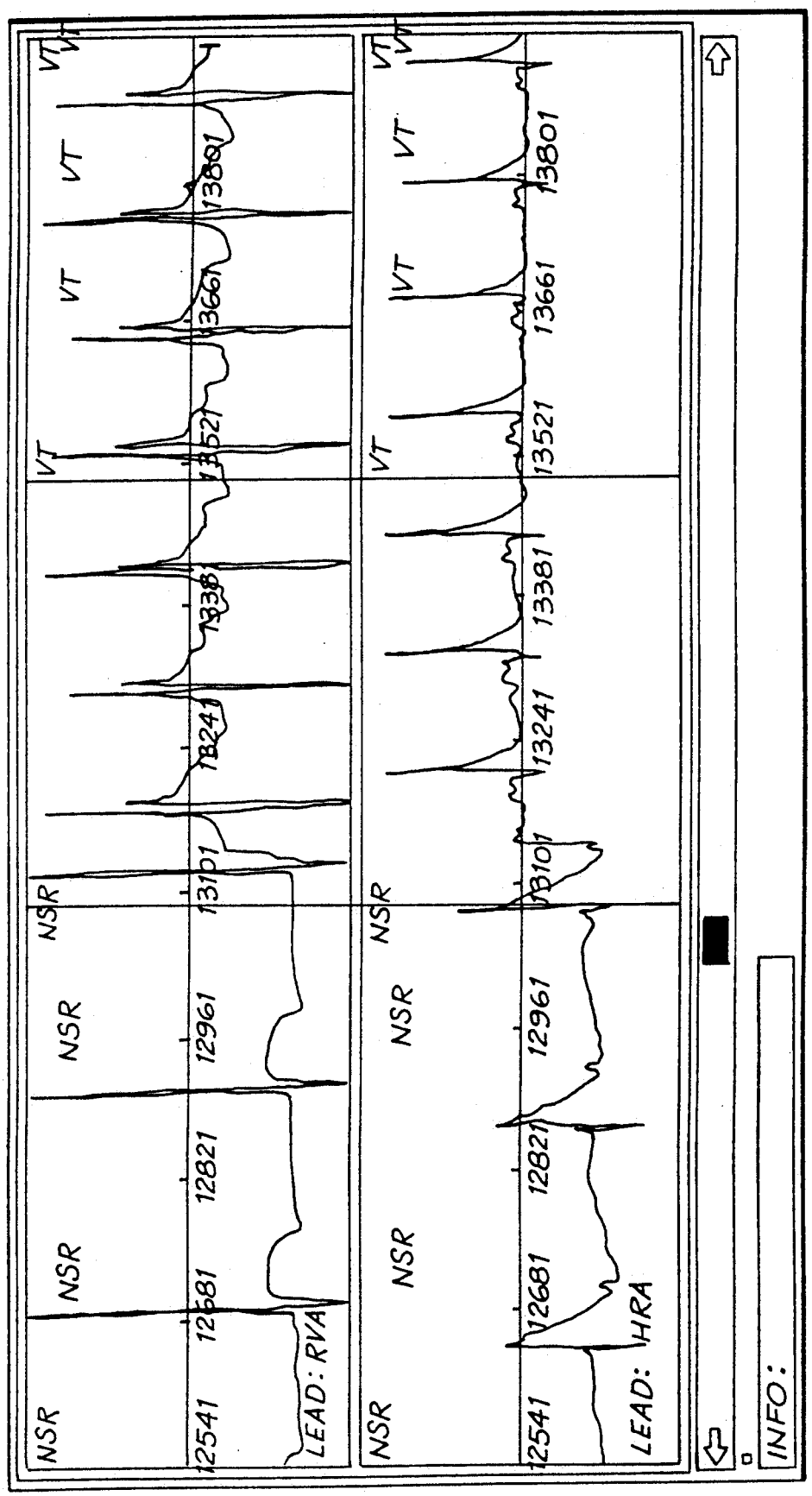
FIG. 10 is a representation of an electrocardiogram showing ventricular tachycardia rhythm with 1:1 retrograde conduction.

FIG. 10 shows a normal rhythm and the RVA morphology change which occurs when 1:1 retrograde ventricular tachycardia is induced.

There were 10 patients with ventricular tachycardia 1:1 and thus requiring morphology analysis. If the neural network morphology logic is not used, the confusion matrix for the ventricular tachycardia 1:1 patients is shown in Table 2.

TABLE 2

| Subclass | Class | Regions | NSR | SVT | VT | VF |
|---|---|---|---|---|---|---|
| NSR | NSR | 10 | 1313 | 0 | 0 | 0 |
| VT 1:1 | VT | 10 | 127 | 894 | 0 | 24 |

Of the 2358 classifications made, 1045 were incorrect (55.7% correct classification). The timing algorithm did not correctly classify any VT 1:1 rhythms since the timing logic requires AV dissociation for a VT classification. FIG. 3).

An additional experiment was conducted to demonstrate the ability of the neural network classifier to store multiple morphologies. The 8 training samples from each of the 10 patients with VT 1:1 were used to form a training set of 80 QRS complexes. A larger network consisting of 10 input neurons, 8 hidden neurons and 1 output neuron was found to produce the best results. After training, the resulting network was used to classify all of the VT 1:1 patients. Thus the network was required to store 20 different morphologies 9 NSR and VT 1:1 for each of the 10 patients). The results, shown in Table 3, show a degraded performance compared with a separate classifier for each patient with 28 misclassified complexes.

TABLE 3

| Subclass | Class | Regions | NSR | SVT | VT | VF |
|---|---|---|---|---|---|---|
| NSR | NSR | 10 | 1252 | 0 | 1 | 0 |
| VT 1:1 | VT | 10 | 0 | 25 | 982 | 0 |

In total, 10315 outputs were produced by the system from the 12483 input QRS complexes (an output is generated only if the X out of Y criterion is satisfied so that the number of outputs is always less than the number of QRS complexes). A total of 39 QRS complexes were incorrectly classified. The incorrect classifications were caused by the following:

Edge Effect (4 complexes). Upon onset of an arrhythmia, latency effects in the X out of Y detector can cause the first complex to be incorrectly classified if the last X complexes were the same. This is not a serious problem as in practice it does not matter if correct classification is delayed by a single QRS complex.

Bad QRS Detection (11 complexes). The QRS detector used was very good, however, there were some cases where it made false detections. Spikes in the waveform could cause false detections or missed detections, causing the system to produce an incorrect classification.

System Errors (24 complexes). The misclassification are due to inadequacies in the system. All of these 24 complexes came from a single patient with sinus tachycardia and were classified as SVT because that patient's NSR morphology was very similar to another patient's VT 1:1 morphology.

Figure 11:
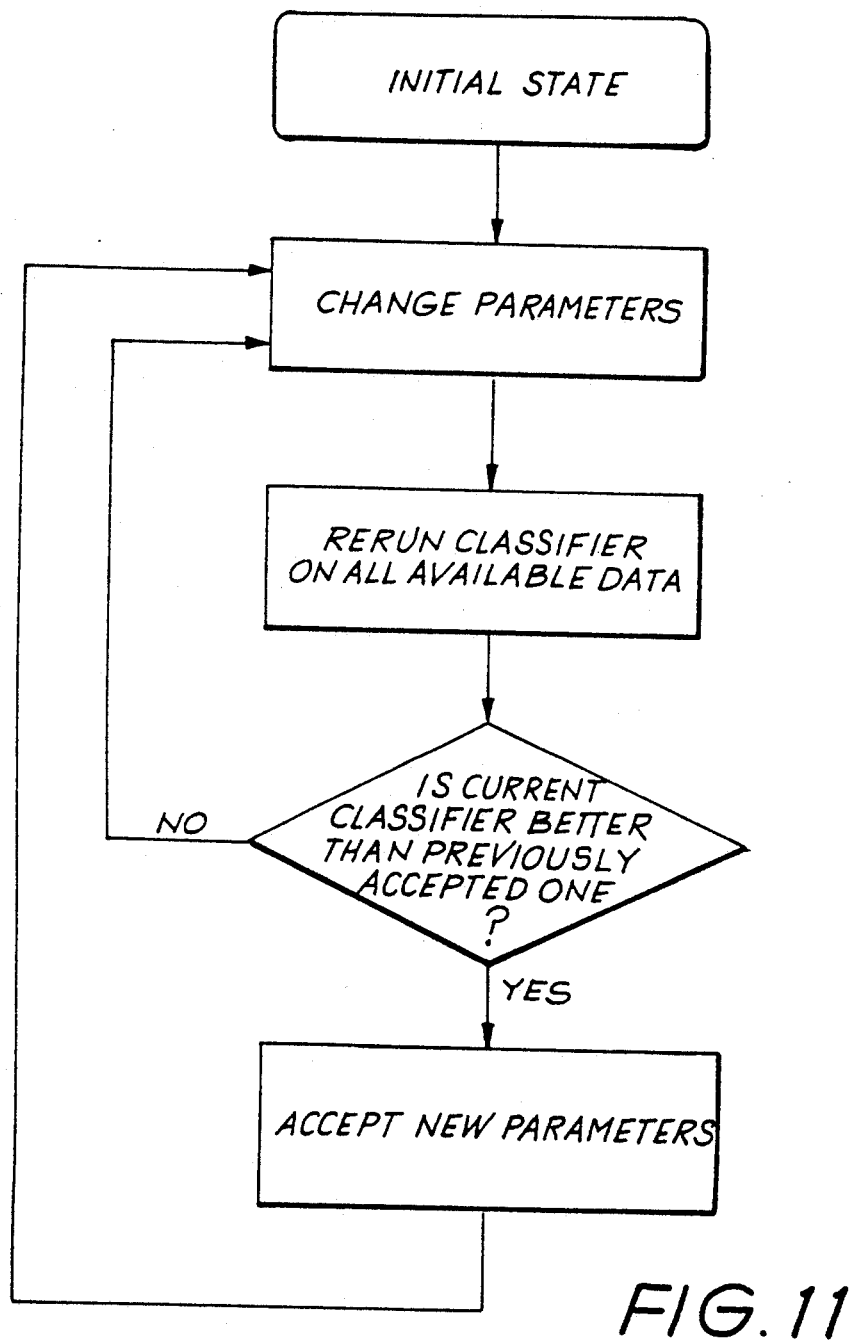
FIG. 11 is a flow chart showing an iterative improvement algorithm for the QRS detector of the embodiment shown in FIG. 2.

The embodiment requires reliable QRS detection to produce a good result as both the alignment of the neural network as well as the timing measurements used by the decision tree assume accurate detection. It is known that the QRS detector could be improved by changing the decay time constant, maximum threshold value and minimum threshold, the detector was automatically tuned using iterative improvement. Iterative improvement starts by classifying the entire data set and noting the number of incorrect classifications. Each parameter in the QRS detector is then altered randomly and the data reclassified using the new QRS detector. If the new classifier performed better than the old one, the new parameters are accepted, otherwise, another random set of parameters are generated and the process repeats itself until no further improvement was seen (see FIG. 11).

Although the invention has been described with reference to a particular embodiment and examples, it should be appreciated that it could be embodied in many other ways. In particular it should be appreciated that the neural network can be used to detect any abnormal morphology. Also, the timing parameters can be changed in a patient dependant manner and thus provide reliable classification for a wide number of patients. The postprocessing logic could be extended using language parsing techniques so that sequences of outputs of the timing and neural network classifiers can be identified and classified correctly. For example, bigeminy can be identified if successive outputs of the timing logic alternate between ventricular tachycardia and supraventricular tachycardia.

What we claim are:

1. A method for automatically classifying intracardiac electrograms, comprising the steps of:
   (a) receiving a first input signal representing an electrogram;
   (b) extracting timing parameters from the first input signal, and deriving from them a first output signal;
   (c) receiving a second input signal representing the electrogram;
   (d) training a neural network using a signal representative of an arrhythmia to recognize that arrhythmia;
   (e) deriving a second output signal, which is a measure of the electrogram's likeness to the signal representative of the arrhythmia, from the second input signal, using the neural network; and
   (f) indicating the classification taking into account the first output signal derived in step (a), and the second output signal derived in step (b).

2. A method according to claim 1, wherein in the step of receiving a first input signal, receiving a first input signal which represents ventricular activity in a first channel and atrial activity in the second channel.

3. A method according to claim 2, wherein in the step of receiving the second input signal, receiving a second input signal which represents ventricular activity.

4. A method according to claim 2, wherein in step (b) extracting the phase difference between the ventricular channel and the atrial channel, determining whether the ratio of this number to the ventricular period is less than a predetermined amount; and indicating, in the first output signal, normal sinus rhythm if the ratio is less than the predetermined amount.

5. A method according to claim 2, wherein in step (b) extracting the periods of the ventricular channel and the atrial channel; determining whether the ratio of the period of the atrial waveform to the period of the ventricular waveform is greater than a predetermined amount; and indicating, in the first output signal, atrial-ventricular dissociation if the ratio is greater than the predetermined amount.

6. A method according to claim 2, wherein in step (b) extracting the ventricular channel period, the atrial channel period, and the phase difference between the ventricular and atrial channels and:
   determining whether the ventricular period is less than a first threshold; and indicating, in the first output signal, ventricular fibrillation if the ventricular period is less than the first threshold;
   determining whether the ventricular period is between the first threshold and a second, higher, threshold and determining whether the ratio of the period of the atrial waveform to the period of the ventricular waveform is greater than a predetermined amount, then indicating, in the first output signal, ventricular fibrillation if the ventricular period is between the first and second thresholds and the ratio is greater than the predetermined amount;
   determining whether the ventricular period is greater than the second threshold and determining whether the ratio of the period of the atrial waveform to the period of the ventricular waveform is greater than a predetermined amount, then indicating, in the first output signal, ventricular tachycardia if the ventricular period is greater than the second threshold and the ratio is greater than the predetermined amount; otherwise,
   determining whether the atrial period is less than a third threshold, between the first and second, then indicating, in the first output signal, supraventricular tachycardia if the atrial period is less than the third threshold;
   determining whether the ratio of the phase difference between the ventricular channel and the atrial channel, and the ventricular period is less than a predetermined amount, and indicating, in the first output signal, normal sinus rhythm if the ratio is less than the predetermined amount;
   otherwise indicating, in the first output signal, supraventricular tachycardia.

7. A method according to claim 6 wherein in step training the neural network with signals representative of normal sinus rhythm and ventricular tachycardia with 1:1 retrograde conduction to recognize normal sinus rhythm and ventricular tachycardia with 1:1 retrograde conduction, and in step (e) deriving a second output signal which is a measure of the electrogram's likeness to the signal representative of ventricular tachycardia with 1:1 retrograde conduction.

8. A method according to claim 7 wherein indicating in step (f) that classification is ventricular tachycardia with 1:1 retrograde conduction if the second output signal indicates a measure of more than a predetermined value of likeness to 1:1 retrograde conduction.

9. A method according to claim 8 including the further step after step (f) of providing a classification indication only when a predetermined number of the immediately preceding classifications indicated in step (f) are the same.

10. A method according to claim 1, wherein step (f) comprises indicating the classification indicated by the first output signal if it indicates ventricular fibrillation arrhythmia; otherwise indicating the classification indicated by the second output signal if the measure of likeness to the signal representative of arrhythmia is greater than a predetermined value, or indicating the classification indicated by the first output signal if the measure of likeness is less than the predetermined value.

11. A system for automatically classifying intracardiac electrograms comprising:
   first signal receiving means to receive a first input signal representing an electrogram; timing classification means to derive a first output signal from timing parameters extracted from the first input signal;

second signal receiving means to receive a second input signal representing the electrogram; a neural network trained using a signal representative of an arrhythmia to recognize that arrhythmia and including means to derive a second output signal which is a measure of the second input signal's likeness to the signal representative of the arrhythmia; and decision means operative, taking into account the first output signal from the timing classification means and the second output signal from the neural network, to indicate the classification.

12. A system according to claim 11 wherein the neural network comprises a multi-layer perceptron.

13. A system according to claim 11 wherein the neural network is trained to recognize normal sinus rhythm and ventricular tachycardia with 1:1 retrograde conduction, and the second output signal is a measure of the electrogram's likeness to a signal representative of ventricular tachycardia with 1:1 retrograde conduction.

14. A system according to claim 11 wherein the first signal receiving means is able to receive a first input signal having two channels and the first input signal represents ventricular activity in a first channel and atrial activity in a second channel.

15. A system according to claim 11 wherein the second input signal represents ventricular activity.

16. A system according to claim 11 wherein the decision means incorporates means to indicate measure whether likeness to the arrhythmia is greater than a predetermined value, and means to indicate the classification indicated by the second output signal when the measure is greater than the predetermined value.

17. A system according to claim 11 wherein the timing classification means includes means to determine ventricular fibrillation arrhythmia, and the decision means incorporates means to indicate the classification indicated by the first output signal if ventricular fibrillation arrhythmia is indicated by the timing classification means; and the decision means includes means to indicate the classification indicated by the second output signal when the measure of likeness to the arrhythmia is greater than a predetermined value, or the classification indicated by the first output signal when the measure of likeness is less than the predetermined value.

18. An implantable cardioverter defibrillator comprising:

first signal receiving means to receive a first input signal representing an electrogram; timing classification means to derive a first output signal from timing parameters extracted from the first input signal;

second signal receiving means to receive a second input signal representing the electrogram; a neural network trained using a signal representative of an arrhythmia to recognize that arrhythmia and including means to derive a second output signal which is a measure of the second input signal's likeness to the signal representative of the arrhythmia; and decision means operative, taking into account the first output signal from the timing classification means and the second output signal from the neural network, to indicate the classification;

wherein the first and second signal receiving means consist of sensing electrodes; and which includes means to use the indicated classification to determine the appropriate therapy to apply.

19. A method for automatically classifying intracardiac electrograms, comprising the steps of:

receiving a first input signal having two channels and representing ventricular activity in a first channel and atrial activity in the second channel;

extracting timing parameters from a first input signal, wherein the timing parameters extracted are the ventricular channel period, the atrial channel period, and the phase difference between the ventricular and atrial channels deriving from the timing parameters a first output signal;

determining whether the ventricular period is less than a first threshold and indicating, in the first output signal, ventricular fibrillation if the ventricular period is lesser than the first threshold;

determining whether the ventricular period is between the first threshold and a second, higher, threshold and determining whether the ratio of the period of the atrial waveform to the period of the ventricular waveform is greater than a predetermined amount; and indicating, in the first output signal, ventricular fibrillation if the ventricular period is between the first and second threshold and the ratio is greater than the predetermined amount;

determining whether the ventricular period is greater than the second threshold and determining whether the ratio of the period of the atrial waveform to the period of the ventricular waveform is greater than a predetermined amount; and indicating, in the first output signal, ventricular tachycardia if the ventricular period is greater than the second threshold and the ratio is greater than the predetermined amount; otherwise, determining whether the atrial period is less than a third threshold, between the first and second; and indicating, in the first output signal, supraventricular tachycardia if the atrial period is less than the third threshold;

determining whether the ratio of the phase difference between the ventricular channel and the atrial channel, and the ventricular period is less than a predetermined amount; and indicating, in the first output signal, normal sinus rhythm if the ratio is less than the predetermined amount;

otherwise indicating, in the first output signal, supraventricular tachycardia.

* * * * *

UNITED STATES PATENT AND TRADEMARK OFFICE
CERTIFICATE OF CORRECTION

PATENT NO. : 5,280,792
DATED : January 25, 1994
INVENTOR(S) : Philip H. W. Leong and Marwan A. Jabri It is certified that error appears in the above-indentified patent and that said Letters Patent is hereby corrected as shown below:

Column 5, line 49 "tha" should be --the--.

Column 6, line 28, "$a^i_i$" should be --$a^i_i$--;
line 52, "$\theta_p$" (first occurrence) should be --$d_p$--.

Column 9, line 46, "ICBG" should be --ICEG--.

Column 12, line 36 (Claim 7, line 1), after "step" insert --(d)--.

Signed and Sealed this

Eighteenth Day of October, 1994

Attest:

BRUCE LEHMAN

Attesting Officer        Commissioner of Patents and Trademarks